US008206746B2

(12) United States Patent
Parikh et al.

(10) Patent No.: US 8,206,746 B2
(45) Date of Patent: *Jun. 26, 2012

(54) MICROPARTICLES OF WATER-INSOLUBLE SUBSTANCES

(75) Inventors: Indu Parikh, Chapel Hill, NC (US); Ulagaraj Selvaraj, Apex, NC (US)

(73) Assignee: Jagotec AG, Muttenz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/260,788

(22) Filed: Sep. 30, 2002

(65) Prior Publication Data
US 2003/0180367 A1    Sep. 25, 2003

Related U.S. Application Data

(63) Continuation-in-part of application No. 09/750,218, filed on Dec. 29, 2000, now Pat. No. 6,465,016, and a continuation-in-part of application No. 09/282,471, filed on Mar. 31, 1999, now Pat. No. 7,255,877, which is a continuation-in-part of application No. 09/218,080, filed on Dec. 22, 1998, now Pat. No. 6,228,399, which is a continuation-in-part of application No. 08/701,483, filed on Aug. 22, 1996, now abandoned.

(51) Int. Cl.
| *A61K 9/14* | (2006.01) |
| *A61K 9/00* | (2006.01) |
| *A61K 9/127* | (2006.01) |
| *A61K 9/16* | (2006.01) |
| *A61K 9/64* | (2006.01) |
| *A61K 9/52* | (2006.01) |
| *A61K 47/32* | (2006.01) |
| *A61F 2/00* | (2006.01) |
| *A61B 8/00* | (2006.01) |
| *B29B 9/00* | (2006.01) |
| *B01F 3/00* | (2006.01) |

(52) U.S. Cl. ........ 424/489; 424/400; 424/450; 424/490; 424/456; 424/457; 424/464; 424/468; 424/493; 424/494; 424/496; 424/497; 424/498; 424/426; 424/9.51; 424/9.52; 264/5; 514/772.4; 252/363.5

(58) Field of Classification Search .................. 424/400, 424/489, 450, 9.51, 9.52, 426, 490, 456, 424/457, 464, 468, 493, 494, 496, 497, 498; 264/5; 514/571; 252/363.5
See application file for complete search history.

(56) References Cited

U.S. PATENT DOCUMENTS

| 2,803,582 | A | 8/1957 | Cherney |
| 3,137,631 | A | 6/1964 | Soloway |
| 3,216,897 | A | 11/1965 | Krantz |
| 3,274,063 | A | 9/1966 | Nieper et al. |
| 3,594,476 | A | 7/1971 | Merrill |
| 3,715,432 | A | 2/1973 | Merrill |
| 3,755,557 | A | 8/1973 | Jacobs |
| 3,794,476 | A | 2/1974 | Michalik et al. |
| 3,937,668 | A | 2/1976 | Zolle |
| 3,960,757 | A | 6/1976 | Morishita et al. |
| 3,965,255 | A | 6/1976 | Bloch et al. |
| 4,016,100 | A | 4/1977 | Suzuki et al. |
| 4,053,585 | A | 10/1977 | Allison et al. |
| 4,056,635 | A | 11/1977 | Glen et al. |
| 4,073,943 | A | 2/1978 | Wretlind et al. |
| 4,078,052 | A | 3/1978 | Papahadjopoulos |
| 4,089,801 | A | 5/1978 | Schneider |
| 4,102,806 | A | 7/1978 | Kondo et al. |
| 4,107,288 | A | 8/1978 | Oppenheim et al. |
| 4,133,874 | A | 1/1979 | Miller et al. |
| 4,137,307 | A * | 1/1979 | Funakoshi et al. ............ 514/21 |
| 4,145,410 | A | 3/1979 | Sears |
| 4,147,767 | A | 4/1979 | Yapel, Jr. |
| 4,186,183 | A | 1/1980 | Steck et al. |
| 4,219,548 | A | 8/1980 | Reller |
| 4,235,871 | A | 11/1980 | Papahadjopoulos et al. |
| 4,241,046 | A | 12/1980 | Papahadjopoulos et al. |
| 4,271,196 | A | 6/1981 | Schmidt |
| 4,298,594 | A | 11/1981 | Sears et al. |

(Continued)

FOREIGN PATENT DOCUMENTS
DE                   2 513 797           10/1975
(Continued)

OTHER PUBLICATIONS

Ross et al., "Aqueous Solutions of Surface-Active Solutes", *Collodial Systems and Interfaces*, © 1988, pp. 148-151. Sande et al., "Antimicrobial Agents: Antifungal and Antiviral Agents", pp. 1219-1222.
Bittman, Robert, "Sterol-Polyene Antibiotic Complexation: Probe of Membrane Structure," *Lipids*, vol. 13, No. 10, pp. 686-691 (1978).
Mishra et al., "Scientifically Speaking: Novel Injectable Formulations of Water-Insoluble Drugs", *Controlled Release Newsletter*, vol. 17, Issue 2, (Jun. 2000), pp. 21-30.
Bangham et al., "Diffusion of Univalent Ions Across the Lamellae of Swollen Phospholipids", *J. Mol. Biol.* (1965) 13, pp. 238-252.
Huang et al., "Interaction of the N-terminus of Sterol Carrier Protein 2 with Membranes: Role of Membrane Curvature", *Biochem. J*, (1999) vol. 8, pp. 593-603.
Gregoriadis, Gregory, "The Carrier Potential of Liposomes in Biology and Medicine", *New Engl. J. Med.*, (1976) vol. 295, No. 13, pp. 704-710.
Cudd et al., "Liposomes Injected Intravenously into Mice Associate with Liver Mitochondria," *Biochem. Biophys Acta*, (1984) vol. 774, pp. 169-180.

(Continued)

*Primary Examiner* — Blessing Fubara
(74) *Attorney, Agent, or Firm* — Mintz Levin Cohn Ferris Glovsky and Popeo, P.C.; Muriel Liberto, Esq.

(57) ABSTRACT

The invention provides a composition comprising microparticles of a water-insoluble or poorly soluble compound, at least one phospholipid, and at least one surfactant, produced by applying an energy to a mixture comprising particles of the compound, the at least one phospholipid, and the at least one surfactant so as to obtain the microparticles. The invention also provides a process for preparing microparticles of a water-insoluble or poorly soluble compound. The process includes mixing particles of a water-insoluble or poorly soluble compound with at least one phospholipid and at least surfactant to form a mixture and applying energy to the mixture sufficient to produce microparticles of the compound. The methods of the invention allow for the production of microparticles smaller than particles produced through previously known methods and the microparticles exhibit advantageous properties including remarkable resistance to particle size growth during storage.

53 Claims, No Drawings

U.S. PATENT DOCUMENTS

| | | | |
|---|---|---|---|
| 4,302,459 A | 11/1981 | Steck et al. | |
| 4,308,166 A | 12/1981 | Marchetti et al. | |
| 4,309,421 A | 1/1982 | Ghyczy et al. | |
| 4,316,884 A | 2/1982 | Alam et al. | |
| 4,320,121 A | 3/1982 | Sears | |
| 4,325,871 A | 4/1982 | Sasaki et al. | |
| 4,328,222 A | 5/1982 | Schmidt | |
| 4,329,332 A | 5/1982 | Couvreur et al. | |
| 4,331,654 A | 5/1982 | Morris | |
| 4,332,795 A | 6/1982 | Ghyczy et al. | |
| 4,332,796 A | 6/1982 | Los | |
| 4,340,594 A | 7/1982 | Mizushima et al. | |
| 4,345,588 A | 8/1982 | Widder et al. | |
| 4,351,831 A | 9/1982 | Growdon et al. | |
| 4,356,167 A | 10/1982 | Kelly | |
| 4,369,182 A | 1/1983 | Ghyczy et al. | |
| 4,371,516 A | 2/1983 | Gregory et al. | |
| 4,378,354 A | 3/1983 | Ghyczy et al. | |
| 4,394,372 A | 7/1983 | Taylor | |
| 4,397,846 A | 8/1983 | Weiner et al. | |
| 4,411,894 A | 10/1983 | Schrank et al. | |
| 4,411,933 A | 10/1983 | Samejima et al. | |
| 4,421,747 A | 12/1983 | Ghyczy et al. | |
| 4,427,649 A | 1/1984 | Dingle et al. | |
| 4,432,975 A | 2/1984 | Libby | |
| 4,448,765 A | 5/1984 | Ash et al. | |
| 4,483,847 A | 11/1984 | Augart | |
| 4,485,054 A | 11/1984 | Mezei et al. | |
| 4,492,720 A | 1/1985 | Mosier | |
| 4,515,736 A | 5/1985 | Deamer | |
| 4,529,561 A | 7/1985 | Hunt et al. | |
| 4,532,089 A | 7/1985 | MacDonald | |
| 4,610,868 A | 9/1986 | Fountain et al. | |
| 4,613,505 A | 9/1986 | Mizushima et al. | |
| 4,622,219 A | 11/1986 | Haynes | |
| 4,629,626 A | 12/1986 | Miyata et al. | |
| RE32,393 E | 4/1987 | Wretlind et al. | |
| 4,675,236 A | 6/1987 | Ohkawara et al. | |
| 4,687,762 A | 8/1987 | Fukushima et al. | |
| 4,725,422 A | 2/1988 | Miyabayashi et al. | |
| 4,756,910 A | 7/1988 | Yagi et al. | |
| 4,758,598 A | 7/1988 | Gregory | |
| 4,761,288 A | 8/1988 | Mezei | |
| 4,762,720 A | 8/1988 | Jizomoto | |
| 4,766,046 A | 8/1988 | Abra et al. | |
| 4,776,991 A | 10/1988 | Farmer et al. | |
| 4,783,484 A | 11/1988 | Violante et al. | |
| 4,800,079 A | 1/1989 | Boyer | |
| 4,801,455 A | 1/1989 | List et al. | |
| 4,803,070 A | 2/1989 | Cantrell et al. | |
| 4,806,350 A | 2/1989 | Gerber | |
| 4,806,352 A | 2/1989 | Cantrell | |
| 4,826,687 A | 5/1989 | Nerome et al. | |
| 4,826,689 A | 5/1989 | Violanto et al. | |
| 4,839,111 A | 6/1989 | Huang | |
| 4,880,634 A | 11/1989 | Speiser | |
| 4,895,726 A | 1/1990 | Curtet et al. | |
| 4,961,890 A | 10/1990 | Boyer | |
| 4,963,367 A | 10/1990 | Ecanow | |
| 4,973,465 A | 11/1990 | Baurain et al. | |
| 5,030,453 A | 7/1991 | Lenk et al. | |
| 5,091,187 A | 2/1992 | Haynes | |
| 5,091,188 A | 2/1992 | Haynes | |
| 5,100,591 A | 3/1992 | Leclef et al. | |
| 5,145,684 A | 9/1992 | Liversidge et al. | |
| 5,164,380 A | 11/1992 | Carli et al. | |
| 5,169,847 A | 12/1992 | Nagy née Kricsfalussy et al. | |
| 5,178,878 A | 1/1993 | Wehling et al. | |
| 5,179,079 A | 1/1993 | Hansen et al. | |
| 5,217,707 A | 6/1993 | Szabo et al. | |
| 5,246,707 A | 9/1993 | Haynes | |
| 5,272,137 A | 12/1993 | Blasé et al. | |
| 5,298,262 A | 3/1994 | Na et al. | |
| 5,302,401 A | 4/1994 | Liversidge et al. | |
| 5,304,564 A | 4/1994 | Tsuboi et al. | |
| 5,320,906 A | 6/1994 | Eley et al. | |
| 5,326,552 A | 7/1994 | Na et al. | |
| 5,336,507 A | 8/1994 | Na et al. | |
| 5,340,564 A | 8/1994 | Illig et al. | |
| 5,346,702 A | 9/1994 | Na et al. | |
| 5,352,459 A | 10/1994 | Hollister et al. | |
| 5,360,593 A | 11/1994 | Bapatia | |
| 5,364,633 A | 11/1994 | Hill et al. | |
| 5,389,377 A | 2/1995 | Chagnon et al. | |
| 5,399,363 A | 3/1995 | Liversidge et al. | |
| 5,447,710 A | 9/1995 | Na et al. | |
| 5,470,583 A | 11/1995 | Na et al. | |
| 5,510,118 A | 4/1996 | Bosch et al. | |
| 5,527,537 A | 6/1996 | Dietl | |
| 5,545,628 A | 8/1996 | Deboeck et al. | |
| RE35,338 E | 9/1996 | Haynes | |
| 5,552,160 A | 9/1996 | Liversidge et al. | |
| 5,560,931 A | 10/1996 | Eickhoff et al. | |
| 5,569,448 A | 10/1996 | Wong et al. | |
| 5,571,536 A | 11/1996 | Eickhoff et al. | |
| 5,576,016 A | 11/1996 | Amselem et al. | |
| 5,578,325 A | 11/1996 | Domb et al. | |
| 5,589,455 A | 12/1996 | Woo | |
| 5,603,951 A | 2/1997 | Woo | |
| 5,631,023 A | 5/1997 | Kearney et al. | |
| 5,637,625 A | 6/1997 | Haynes | |
| 5,639,474 A | 6/1997 | Woo | |
| 5,645,856 A | 7/1997 | Lacy et al. | |
| 5,656,289 A | 8/1997 | Cho et al. | |
| 5,660,854 A * | 8/1997 | Haynes et al. | 424/450 |
| 5,660,858 A | 8/1997 | Parikh et al. | |
| 5,662,932 A | 9/1997 | Amselem et al. | |
| 5,663,198 A | 9/1997 | Reul et al. | |
| 5,676,928 A | 10/1997 | Klaveness et al. | |
| 5,776,491 A | 7/1998 | Allen, Jr. et al. | |
| 5,776,495 A | 7/1998 | Duclos et al. | |
| 5,785,976 A * | 7/1998 | Westesen et al. | 424/400 |
| 5,820,861 A * | 10/1998 | O'Rand et al. | 424/184.1 |
| 5,827,536 A | 10/1998 | Laurelle | |
| 5,827,822 A | 10/1998 | Floc'h et al. | |
| 5,834,025 A | 11/1998 | de Garavilla et al. | |
| 5,851,275 A | 12/1998 | Amidon et al. | |
| 5,858,398 A | 1/1999 | Cho | |
| 5,858,410 A | 1/1999 | Muller et al. | |
| 5,880,148 A | 3/1999 | Edgar et al. | |
| 5,922,355 A | 7/1999 | Parikh et al. | |
| 5,932,243 A | 8/1999 | Fricker et al. | |
| 5,972,366 A | 10/1999 | Haynes et al. | |
| 5,976,577 A | 11/1999 | Green et al. | |
| 6,045,829 A | 4/2000 | Liversidge et al. | |
| 6,046,163 A | 4/2000 | Stuchlik et al. | |
| 6,057,289 A | 5/2000 | Mulye | |
| 6,063,762 A | 5/2000 | Hong et al. | |
| 6,086,376 A | 7/2000 | Moussa et al. | |
| 6,096,338 A | 8/2000 | Lacy et al. | |
| 6,136,061 A * | 10/2000 | Gibson | 75/231 |
| 6,177,103 B1 | 1/2001 | Pace et al. | |
| 6,228,399 B1 | 5/2001 | Parikh et al. | |
| 6,267,989 B1 | 7/2001 | Liversidge et al. | |
| 6,270,806 B1 | 8/2001 | Liversidge et al. | |
| 6,337,092 B1 | 1/2002 | Khan et al. | |
| 6,387,409 B1 | 5/2002 | Khan et al. | |
| 6,465,016 B2 * | 10/2002 | Parikh et al. | 424/489 |
| 6,696,084 B2 * | 2/2004 | Pace et al. | 424/451 |
| 7,255,877 B2 * | 8/2007 | Parikh | 424/489 |
| 7,939,105 B2 * | 5/2011 | Parikh et al. | 424/490 |
| 7,939,106 B2 * | 5/2011 | Parikh et al. | 424/490 |

FOREIGN PATENT DOCUMENTS

| | | |
|---|---|---|
| DE | 2 938 807 | 11/1980 |
| DE | 3 421 468 | 12/1985 |
| DE | 4 440 337 | 5/1996 |
| EP | 0 052 322 | 5/1982 |
| EP | 0 193 208 | 9/1986 |
| EP | 0 272 091 | 6/1988 |
| EP | 0 391 369 | 4/1990 |
| EP | 0 153 926 | 2/1991 |
| EP | 0 418 153 | 3/1991 |
| EP | 0 456 670 | 11/1991 |
| EP | 0 456 764 | 11/1991 |
| EP | 0 499 299 | 8/1992 |
| EP | 0 330 532 | 12/1992 |

| | | |
|---|---|---|
| EP | 0 570 829 | 5/1993 |
| EP | 0 580 690 | 2/1994 |
| EP | 0 601 618 | 6/1994 |
| EP | 0 602 700 | 6/1994 |
| EP | 0 687 172 | 12/1995 |
| EP | 0 605 497 | 3/1996 |
| EP | 0 724 877 | 8/1996 |
| EP | 0 757 911 | 2/1997 |
| FR | 2 617 047 | 12/1988 |
| GB | 2046094 | 10/1978 |
| GB | 1 527 638 | 3/1996 |
| HU | 211 580 B | 6/1995 |
| JP | 56167616 | 5/1980 |
| JP | 1502590 | 11/1980 |
| JP | 55141407 | 11/1980 |
| JP | 60208910 | 11/1980 |
| JP | 63233915 | 10/1985 |
| JP | 63502117 | 9/1986 |
| WO | WO 85/00011 | 1/1985 |
| WO | WO 87/04592 | 8/1987 |
| WO | WO 88/04924 | 7/1988 |
| WO | WO-90/07491 A1 | 7/1990 |
| WO | WO 91/04011 | 4/1991 |
| WO | WO 91/16068 | 10/1991 |
| WO | WO 92/18105 | 10/1992 |
| WO | WO 93/05768 | 4/1993 |
| WO | WO 94/20072 | 9/1994 |
| WO | WO 96/21439 | 7/1996 |
| WO | WO 96/24332 | 8/1996 |
| WO | WO 97/14407 | 4/1997 |
| WO | WO 98/07414 | 2/1998 |
| WO | WO 98/41239 | 9/1998 |
| WO | WO 99/29300 | 6/1999 |
| WO | WO 99/29316 | 6/1999 |
| WO | WO 99/49846 | 10/1999 |
| WO | WO 99/49848 | 10/1999 |
| WO | WO 99/61001 | 12/1999 |
| WO | WO 99/65469 | 12/1999 |
| WO | WO 00/10531 | 3/2000 |
| WO | WO 00/30615 | 6/2000 |
| WO | WO 00/30616 | 6/2000 |
| WO | WO 00/40219 | 7/2000 |
| WO | WO 00/41682 | 7/2000 |
| WO | WO 01/21154 | 3/2001 |
| WO | WO 01/30372 | 5/2001 |

OTHER PUBLICATIONS

Benz et al., "Electrical Capacity of Black Lipid Films and of Lipid Bilayers Made from Monolayers", *Biochem. Biophys. Acta*, (1975) vol. 394, pp. 323-334.

Goodman and Gillman's, "The Pharmacological Basis of Therapeutics," 7th Ed., *MacMillan Publishing Co.*, New York (1985) Chap. 15, p. 312.

Cherney, L.S., "Tetracaine Hydroiodide: A Long Lasting Local Anesthetic Agent for the Relief of Postoperative Pain", *Anesth. Analg.* (1963) vol. 42, No. 4, pp. 477-481.

Haynes et al., "Metal-Ligand Interactions in Organic Chemistry and Biochemistry", *B. Pullman and N. Goldblum (eds.)*, part 2, (1977), pp. 189-212.

Haynes et al., "Ultra-Long Duration Local Anesthesia Produced by Injection of Lecithin-coated Methoxyflurane Microdroplets", *Anesthesiology* (1985) vol. 63, No. 5, pp. 490-499.

Haynes et al., "Ultra-Long Duration Local Anesthesia Produced by Intra-Dermal Injection of Lecithin-Coated Methoxyflurane Microdroplets", *Proceed. Intern. Symp. Control. Rel. Bioact. Mater.*, (1987) vol. 14, pp. 293-294.

Kirkpatrick et al., "Local Anesthetic Efficacy of Methoxyflurane Microdroplets in Man," *Anesthesiology* (1987) 67(3A): A254.

Gennaro et al., "Sustained-Release Drug Therapy," *Remington's Pharmaceutical Sciences*, 17th Ed., (1985), p. 1645.

"Derived Diameters and Distribution Statistics," from an unknown web-site, 6 pages.

Freitas et al., "Spray Drying of Solid Lipid Nanoparticles (SLN™)", *Elsevier Science*, 1998, pp. 145-151.

"Getting Started", Man 0106, Issue 1.0, (Jan. 1996), *Malvern Instruments Ltd.*, England, pp. 7.1-7.7.

Chulia et al., Powder Technology and Pharmaceutical Processes, (1994), pp. 66-67.

Herbert A. Leiberman and Leon Lachman, Eds., *Pharmaceutical Dosage Forms*, Tablets, vol. 1, (1980), p. 13.

Kawashima, Yoshiaki, "Preparation of Powdered Phospholipid Nanospheres by Spray Drying in an Aqueous System with Sugars", *Chem. Pharm. Bull.* 40 (7), 1992, pp. 1911-1916.

Miyajima, Koichiro, "Role of Saccharides for the Freeze-Thawing and Freeze-Drying of Liposome", *Advanced Drug Delivery Review*, vol. 24, (1997), pp. 151-159.

Buchmuller et al., "Cryopel: Ein neus Verfahren zum Pelletieren und Frosten Biologischer Substrate," *Gas Aktuell*, 35, 1(989), pp. 10-13.

Wu et al., "Pharmacokinetics of Methoxyflurane After Its Intra-Dermal Injection as Lecithin-Coated Microdroplets,"*Journal of Controlled Release*, (1989), vol. 9, pp. 1-12.

Pace et al., "Novel Injectable Formulations of Insoluble Drugs", *Pharmaceutical Technology*, vol. 23, No. 3, (Mar. 1999), pp. 116-134.

Rompp's Chemie Lexikon, 2 Aufl., Bd. 1, (1950), Stichwort, "Emulsion".

Bergmann, Ludwig, *Der Ultraschall*, 5 Aufl., (1949), Stuttgart, S. 551-564, 672f.

Lehninger Biochemistry, "The Molecular Basis of Cell Structure and Function", (1970) Chapter 10.

Guzman et al., 1088 J. Pharm. Sci 82 (1993) No. 5 pp. 498-502 Formation and Characterization of Cyclosporine-Loaded Nanoparticles.

Napper, "Polymeric Stabilizations of Colloidal Dispersions", (1983).

Muller et al., Emulsions and Nanosuspension, Chap. 9 (1998) p. 163.

Lourenco et al., Int. J. of Pharm. 138 (1996), 1-12, "Steric stabilization of nanoparticles:size and surface properties".

Luckham Pestic. Sci., 1989, 25, 25-34, "The Physical Stability of Suspension Concentrates with Particular etc."

Calvor et al. Pharm. Dev. Tech., 3(3), 297-205, 1998, "Production of Microparticles by High Pressure etc."

[LSP4]La Fuma Polymery 1998 43 nr 2, 104-108, "The role of water-soluble polymers at the solid/liquid etc."

Website http://userpage.fu-berlin.de/~kayser/nanosuspensionen.htm.

Siekmann et al. Pharm. Pharmacol Lett (1994) 3:225-228 "Melt-homogenized Solid Lipid Nanparticles Stabilized by the Non-ionic Surfactant Tyloxapol".

Muller et al., "Nanosuspensions for the I.V. Administration of Poorly Soluble Drugs-Stability During Sterilization and Long-Term Storage", Dept. of Pharmaceutics, Biopharmaceutics and Biotechnology, The Free University of Berlin, Kelchstraβe 31, D-12169 Berlin, Germany.

Zuidam et al."Sterilization of Liposomes by Heat Treatment", Pharmaceutical Research, vol. 10, No. 11, 1993 p. 1591-1596.

* cited by examiner

MICROPARTICLES OF WATER-INSOLUBLE SUBSTANCES

CROSS REFERENCE TO RELATED PATENT APPLICATIONS

This patent application is a continuation-in-part of U.S. patent application Ser. No. 09/750,218, filed Dec. 29, 2000 now U.S. Pat. No. 6,465,016, and U.S. patent application Ser. No. 09/282,471, filed Mar. 31, 1999 now U.S. Pat. No. 7,255,877, which is a continuation-in-part of U.S. patent application Ser. No. 09/218,080, filed Dec. 22, 1998, now U.S. Pat. No. 6,228,399, which is a continuation-in-part of U.S. patent application Ser. No. 08/701,483, filed Aug. 22, 1996 now abandoned. The disclosures of all of these patent applications are hereby incorporated by reference.

FIELD OF THE INVENTION

This invention relates to compositions of sub-micron and micron sized particles of water-insoluble or poorly soluble compounds and methods for making the same.

BACKGROUND OF THE INVENTION

Useful preparations of water-insoluble or poorly soluble substances are needed in the pharmaceutical industry. Particularly desired are formulations of water-insoluble or poorly soluble drugs that are stable when dispersed in water, in lyophilized form, or when spray-dried.

Current technology for administering formulations of insoluble drugs, described in, for example, U.S. Pat. Nos. 5,091,188; 5,091,187 and 4,725,442, is directed to either (a) coating small drug particles with natural or synthetic phospholipids or (b) dissolving the drug in a suitable lipophilic carrier and forming an emulsion stabilized with natural or semisynthetic phospholipids. One of the disadvantages of these formulations is that certain drug particles in suspension tend to grow over time because of the dissolution and reprecipitation phenomenon known as "Ostwald ripening." See, e.g., Luckham, *Pestic. Sci.*, (1999) 25, 25-34.

For these and other reasons, there remains a need for improved and alternative formulations of water-insoluble and poorly soluble substances. The invention provides such compositions and methods of producing and using the same. These and other advantages of the invention, as well as additional inventive features, will be apparent from the description of the invention provided herein.

BRIEF SUMMARY OF THE INVENTION

The invention provides a composition comprising microparticles of a water-insoluble or poorly soluble compound, at least one phospholipid, and at least one surfactant, produced by a method comprising applying an energy to a mixture comprising particles of the compound, the at least one phospholipid, and the at least one surfactant so as to obtain the microparticles. The invention also provides a method of producing microparticles comprising applying energy (e.g., by precipitation, microfluidization, or both) to a mixture comprising particles of the compound, at least one surfactant, and at least one phospholipid, so as to obtain microparticles of the compound. In a particular aspect, the at least one surfactant of the composition or the method is not a phospholipid. Additional inventive aspects of the compositions and methods of the invention are provided in the following detailed description of the invention.

DETAILED DESCRIPTION OF THE INVENTION

This invention relates to procedures that yield stable microparticles (sub-micron and micron-sized particles) of water-insoluble or poorly soluble drugs or other industrially useful insoluble compounds and compositions produced by such procedures. In order to achieve the advantages of the present invention, it is necessary that the phospholipid(s) and the surfactant(s) both be present at the time of particle size reduction or precipitation. Accordingly, the following description of the invention is focused on methods for preparing submicron to micron size particles using a combination of surface modifier(s) and phospholipid(s) and the stable microparticles obtained by such methods.

In one aspect, the invention provides a process for preparing microparticles (i.e., sub-micron and micron sized particles) of a water-insoluble or poorly soluble compound that includes the steps of (1) mixing particles of a water-insoluble or poorly soluble industrially useful compound with a phospholipid and at least one surfactant and (2) thereafter applying energy to the mixture so as to obtain the microparticles. The inventors have discovered that much smaller particles are produced when an energy input is applied in the presence of a surfactant and a phospholipid, as compared to the phospholipid alone, and that microparticles produced in accordance with the invention do not significantly increase in size over significant periods of time.

As used herein, the term "microparticle" refers to particles having a diameter of between 1 nm and 1 micrometer. Microparticles of the invention include solid particles of irregular, non-spherical, or spherical shapes. Microparticles produced by applying an input of energy to particles of the water insoluble or poorly soluble compound with a surfactant (surface modifier) or combination of surfactants in addition to a phospholipid or combination of phospholipids are unexpectedly smaller, usually about 50% smaller, or even more than about 50% smaller, than particles of the water-insoluble or poorly soluble compound prepared with the same phospholipid in the absence of the surface modifier(s). Thus, the invention provides microparticles of a water-insoluble or poorly soluble compound that can be characterized by having a volume weighted mean particle size that is at least 50%, and preferably about 50-90%, smaller than particles obtained using the same energy input and phospholipid alone (i.e., without the use of a surfactant). The surprising discovery that such a significant reduction in the particle size of water-insoluble and poorly soluble compounds is achievable with the addition of one or more surfactants and one or more phospholipids during size reduction is an important aspect of the invention. A remarkable resistance to particle size growth on storage is another important characteristic of microparticles of the invention.

Compositions of the invention include combinations of natural or synthetic phospholipids, and one or more non-ionic, anionic or cationic surfactants coated or adhered to the surfaces of the water insoluble-compound or poorly water-soluble ("poorly soluble") microparticles. Water insoluble and poorly insoluble compounds are compounds having poor solubility in water: that is <5 mg/ml at physiological pH (6.5-7.4). Preferably, the water insoluble compound in a composition of the invention has a solubility of <1 mg/ml, more preferably <0.1 mg/ml, or even less than 0.1 mg/ml, at physiological pH.

In another aspect, the invention provides a process of stabilizing microparticles and preventing microparticles from aggregating or flocculating by coating or adhering onto the surfaces of the particles of a water-insoluble or poorly soluble compound (e.g., cyclosporine particles) a mixture of a phospholipid together with at least one non-ionic, anionic or cationic second surface modifier. The steps of the process specifically include mixing the particles of the water-insoluble or poorly soluble compound (e.g., cyclic oligopeptide cyclosporine) with a phospholipid and at least one non-ionic, anionic or cationic second surface modifier (surfactant), and thereafter applying energy to the mixture sufficient to produce microparticles having volume-weighted mean particle size values that are about 50% smaller than particles produced without the presence of the second surface modifier using the same energy input.

In yet another aspect, the invention provides microparticles that consist essentially of a solid core of a water-insoluble or poorly soluble coated with a combination of phospholipid(s) and surface modifier(s), wherein the microparticles are characterized in having a volume-weighted mean particle size value that is about 50% smaller than the volume-weighted mean particle size value of particles of the compound produced in the presence of the phospholipid(s) without the surface modifier(s), applying the same energy input.

In still another aspect, the invention provides microparticles that consist essentially of a solid core of a water-insoluble or poorly soluble compound coated with a combination of phospholipid(s) and surface modifier(s). The invention also provides microparticles that consist essentially of a solid water-insoluble or poorly soluble compound core stabilized by a combination of one or more phospholipids and one or more surface modifiers adhering to or coated on the surface of the core.

Industrially useful water insoluble or poorly soluble compounds include biologically useful compounds, imaging agents, and pharmaceutically useful compounds, such as drugs for human and veterinary medicine. Examples of some preferred water-insoluble drugs include immunosuppressive agents such as cyclosporine including cyclosporine A, immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antiarrhythmics, antihypertensive agents, antineoplastic agents, hormones, and nutrients. A detailed description of these and other suitable drugs may be found in *Remington's Pharmaceutical Sciences*, 18$^{th}$ edition, 1990, Mack Publishing Co. Philadelphia, Pa.

Microparticles of the invention can include a water-insoluble or poorly soluble compound in a solid core, which core can include an amorphous solid, a crystalline solid, or a mixture of amorphous and crystalline solids in the microparticle core. A composition can include a mixture of water-insoluble or poorly soluble compounds. For example, the water-insoluble or poorly soluble compound can be a single stereoisomer of a water-insoluble or poorly soluble compound, a mixture of stereoisomers, a racemic mixture of stereoisomers, a diastereomeric mixture of isomers, or a combination of optical isomers of a single compound homolog.

Phospholipid(s) and surface modifier(s) can be adsorbed onto the surfaces of the water insoluble or poorly soluble particles (e.g., particles including a solid core of a water-insoluble or poorly soluble drug, such as cyclosporine) in sufficient quantity to retard drug particle growth; reduce drug average particle size from 5 to 100 μm to sub-micron and micron size particles by one or more methods known in the art, such as sonication, homogenization, milling, microfluidization, precipitation (e.g., precipitation from supercritical fluid), and recrystallization; and maintain sub-micron and micron size particles on subsequent storage in suspension or in solid dosage form. The concentration of phospholipid or surface modifier in the suspension or solid dosage form can be present in the range of 0.1 to 50%, preferably 0.2 to 20%, and more preferably 0.5 to 10%. The concentrations of surface modifiers used in the process described here are normally above their critical micelle concentrations (CMC) and hence facilitate the formation of sub-micron to micron particles by stabilizing the particles. Microparticles of the invention can be characterized by a ratio of phospholipid to total amount of surfactant of about 100:1 to about 1:1, preferably from about 10:1 to about 2:1. The ratio of water-insoluble or poorly soluble compound to phospholipid can range from 1:10 to about 10:1, preferably from 1:5 to about 5:1. Water-insoluble or poorly soluble compound concentrations in a composition of the invention can range from about 1% to about 90%, preferably about 2% to about 20%, and more preferably from about 2% to about 10% of the composition. An especially preferred concentration is about 5%.

Any natural or synthetic phospholipid, for example phosphatidylcholine, phosphatidylethanolamine, phosphatidylserine, phosphatidylinositol, phosphatidylglycerol, phosphatidic acid, lysophospholipids, egg or soybean phospholipid (e.g., egg phosphatidylcholine), purified or enriched fractionated or partially purified extracts of natural phospholipids such as purified or enriched or fractionated or partially purified egg derived phospholipids, e.g., Lipoid E80, or a combination of any thereof can be included or used in the compositions and methods of the invention. The phospholipid may be salted or desalted; hydrogenated or partially hydrogenated; and natural, semisynthetic, or synthetic. Examples of commercially available phospholipids include, but are not limited to, egg phospholipids P123 (Pfanstiehl), Lipoid E80 (Lipoid); and hydrogenated soy phospholipids Phospholipon 90H and 100H (Natterman) and 99% pure soy phosphatidyl choline (Avanti Polar Lipids).

In one aspect, the phospholipid can be selected from the group consisting of phospholipid of egg origin, phospholipid of plant origin, a semisynthetic phospholipid, a synthetic phospholipid, a phospholipid in partly hydrogenated form, a phospholipid in fully hydrogenated form, a phospholipid in desalted form, a phospholipid salt, phosphatidylcholine, dimyristoyl phosphatidylglycerol sodium salt, phosphatidylethanolamine, phosphatidylserine, phosphatidic acid, a lysophospholipid, or a combination thereof. The phospholipid can also be a phospholipid salt, phosphatidylcholine, dimyristoyl phosphatidylglycerol sodium salt, or combination thereof. In another sense the phospholipid can be phosphatidyl glycerol, phosphatidyl inosite, phosphatidylserine, or phosphatidic acid, their biocompatible salts, or combinations of any thereof. In another exemplary aspect, the phospholipid can be selected from the group consisting of a phospholipid of egg origin, a phospholipid of plant origin, a semisynthetic phospholipid, a synthetic phospholipid, a phospholipid in partly hydrogenated form, a phospholipid in fully hydrogenated form, a phospholipid in desalted form, a phospholipid salt, phosphatidylcholine, dimyristoyl phosphatidylglycerol sodium salt, phosphatidylethanolamine, phosphatidylserine, phosphatidic acid, a lysophospholipid, or a combination thereof, with the proviso that the second surface modifier is not a phospholipid.

The process of the invention can be performed with non-ionic, anionic, or cationic surfactants. Examples of some suitable surfactants include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan ethers, sorbitan fatty acid esters, polyoxyethylene fatty acids esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxypropylcellulose, hydroxypropylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, chitosans and lauryldimethylbenzylammonium chloride, (e) colloidal clays such as bentonite and veegum, or a combination thereof. A detailed description of these surfactants may be found in Remington's Pharmaceutical Sciences, and Theory and Practice of Industrial Pharmacy, Lachman et al, 1986. More specific examples of suitable surface modifiers include one or combination of the following surfactants: poloxamers, such as Pluronic™ F68, F108, and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylenediamine available from BASF, Triton™ X-200, which is an alkyl aryl polyether sulfonate, available from Rohm and Haas. Tween 20, 40, 60 and 80, which are polyoxyethylene sorbitan fatty acid esters, available from ICI Specialty Chemicals, polyoxyethylene stearate (Myrj 52) available from ICI Specialty Chemicals, Carbowax™ 3550 and 934, which are polyethylene glycols available from Union Carbide, hydroxy propylmethylcellulose, dimyristoyl phosphatidylglycerol sodium salt, sodium dodecylsulfate, sodium deoxycholate, and cetyltrimethylammonium bromide.

In a particular aspect, the surface modifier is selected from the a polyoxyethylene sorbitan fatty acid ester, a block copolymer of ethylene oxide and propylene oxide, polyoxyethylene stearate, a tetrafunctional block copolymer derived from sequential addition of ethylene oxide and propylene oxide to ethylenediamine, an alkyl aryl polyether sulfonate, polyethylene glycol, sodium dodecylsulfate, sodium deoxycholate, cetyltrimethylammonium bromide, or a combination of any thereof.

In some cases, preferably at least two surfactants are used in the production of the microparticles of the invention. Thus, in one aspect the invention provides a composition comprising at least two second surface modifiers in addition to the phospholipid or phospholipid(s) and water-insoluble or poorly soluble compound microparticles.

When two second surfactants or surface modifiers are used in addition to a phospholipid or more than one phospholipid to stabilize microparticles according to the invention, the ratio of the primary and secondary second surface modifiers can range from about 1 part of said primary second surface modifier to 999 parts of said secondary second surface modifier to about 999 parts of said primary second surface modifier to 1 part of said secondary second surface modifier, preferably from about 1 part of said primary second surface modifier to 99 parts of said secondary second surface modifier to about 99 parts of said primary second surface modifier to 1 part of said secondary second surface modifier, more preferably from about 1 part of said primary second surface modifier to 9 parts of said secondary second surface modifier to about 9 parts of said primary second surface modifier to 1 part of said secondary second surface modifier. Up to and including equal amounts of primary and secondary surface modifiers can be used. In another aspect more than two secondary surface modifiers can be used wherein the ratio of any two is in the just described distribution of ratios, up to and including equal amounts of each.

In a particular aspect of the invention, the second surface modifier can be selected from the group of negatively charged phospholipids, for example negatively charged phospholipids consisting of phosphatidyl glycerol, phosphatidyl inosite, phosphatidylserine, phosphatidic acid and their salts. A preferred charged phospholipid in this respect is dimyristoyl phosphatidylglycerol sodium salt. In yet another aspect of this invention, the surface modifier is not a phospholipid. Thus, compositions and methods of the invention can be characterized by the proviso that the surfactant or surface modifier is not a phospholipid.

In a preferred aspect of the invention, when free-flowing formulations are desired, the second surfactant(s) or surface modifier(s) will itself be a powder.

Preferred second surface modifiers also can include one or more members of the group consisting of Tween 80, Tween 20, Pluronic F68, Tetronic T908, Myri 52, sodium deoxycholate, and combinations thereof. Preferred surface modifiers can further include one or more members of the group consisting of Tween 80, Tween 20, Pluronic F68, Tetronic T908, Myri 52, and cetyl trimethylammonium bromide.

As exemplified by the foregoing passages, considerable variations as to the identities and types of phospholipid and especially the surfactant or surfactants (surface active agents or surface modifiers) can be expected depending upon the compound, drug, or active agent in the composition, as the surface properties of these compositions can differ significantly. The most advantageous surface active agent for a water-insoluble or poorly soluble compound will be apparent following empirical tests to identify the surfactant or surfactant system/combination resulting in the requisite particle size and particle size stability on storage over time.

As mentioned above, various procedures can be used to produce these stable sub-micron and micron size particles including mixing the insoluble substance with phospholipid and surfactant(s) followed by sonication, milling, homogenization, microfluidization; or precipitating the microparticles from a solution of the substance, phospholipid(s), and surfactant(s) using antisolvent and solvent precipitation in the presence of phospholipid(s) and second surface modifiers (i.e., the surfactant(s)).

The combination of phospholipids and surfactants allows the formation and stabilization of the sub-micron and micron size compound particles via hydrophilic, lipophilic and electrostatic interactions and therefore prevent these particles from aggregation or flocculation. It further appears that the phospholipid(s) and surfactant(s), adsorb or adhere to the surfaces of particles of the compound, convert lipophilic to hydrophilic surfaces with increased steric hindrance/stability, and possibly modify zeta potential of surfaces with more charge repulsion stabilization. It also is thought that some of the other functions of the second surface modifier(s) as it relates to this invention include (a) suppressing the process of Ostwald Ripening and therefore maintaining the particle size; (b) increasing the storage stability, minimizing sedimentation, and decreasing the particle growth during lyophilization and reconstitution; (c) adhering or coating firmly onto the surfaces of water-insoluble drug particles and therefore modifying the interfaces between the particles and the liquid in the resulting formulations; (d) increasing the interface compatibility between water-insoluble drug particles and the liquid; (e) possibly orienting preferentially themselves with the hydrophilic portion sticking into the aqueous solution and the lipophilic portion strongly adsorbed at the water-insoluble drug particle surfaces.

Formulations containing drug microparticles of the invention provide specific advantages over non-micronized drug particles, including providing improved oral bioavailability of drugs that are poorly absorbed from GI tract, allowing the development of injectable formulations of drugs that are currently available only in oral dosage form, providing injectable formulations of drugs that are currently prepared with organic solvents, providing sustained release of intramuscular injectable drugs that are currently administered through daily injection or constant infusion, and allowing the preparation of inhaled or ophthalmic formulation of drugs that otherwise could not be formulated for nasal or ocular use. Particles and formulations of particles of water-insoluble drugs stabilized by a combination of one or more surface modifier(s) together with one or more phospholipid(s) exhibit enhanced storage stability over particles and formulations of particles of the drug stabilized by the phospholipid in the absence of the surface modifier(s). The size of the final dosage form of pharmaceutical microparticle compositions produced according to the inventive methods described herein can be significantly smaller than the currently marketed forms of such drugs.

Formulations prepared by the invention may be dried by lyophilization, fluid drying, or spray drying. Such dried powder formulations can be resuspended or filled into capsules or converted into granules or tablets with the addition of binders and other excipients known in the art. Compositions of the invention can take a dispersed form, a lyophilized form, or a spray-dried form. The invention also provides free-flowing powders of poorly soluble or insoluble drug substances, such as cyclosporine, as well as solid dosage forms of these powders, for instance in the form of compressed tablets and the like. Surprisingly, the inventors have found that such microparticulate formulations exhibit enhanced stability and bioavailability. Mannitol and other agents may be added to adjust the final formulation to isotonicity as well as acting as a stabilizing aid during drying. Pharmaceutical compositions of the invention can be formulated for injectable, ophthalmic, oral, inhalation, ocular, nasal, or injectable administration. Particular pharmaceutical compositions of the invention are formulated in injectable form for intravenous, intra-arterial, intra-muscular, intradermal, subcutaneous, intra-articular, cerebrospinal, epidural, intracostal, intraperitoneal, intratumor, intrabladder, intra-lesion, or subconjunctival administration. Compositions of the invention can be formulated as a hard or soft gel capsules. Compositions of the invention also can be in the form of suspensions, especially suspensions in an aqueous medium such as water, water for injection, buffered water, phosphate buffered saline, and other pharmaceutically acceptable aqueous media. Alternatively, the compositions of this invention can be in the form of dried powders that are substantially free of water (e.g., at least 98% free of water). The powders can be further manipulated to form tablets, capsules, suspensions, creams, ointments, pills, suppositories, and other useful and pharmaceutically acceptable dosage forms.

As mentioned elsewhere herein, formulations prepared by this invention can be useful as pharmaceutical compositions and may be dried, e.g., by lyophilization, fluid or spray drying, evaporation, or other known methods, into powders. Optionally, compositions of the invention can be so dried in the presence of one or more excipients such as carbohydrates such as sugars (e.g., mannitol), salts such as buffering salts and salts that can produce isotonic formulations, dispersing aids, binders and the like, which dried powders can be resuspended or filled into capsules (e.g., hard gel or soft gel capsule dosage formulations) or converted into granules or tablets with the addition of binders such as polyvinylpyrrolidone and other excipients such as magnesium stearate and silica known in the art. Compositions of the invention can be provided in other pharmaceutically acceptable dosage forms such as tablets, capsules, suspensions, lozenges, pills and the like. Dosage forms of such pharmaceutically acceptable compositions may contain additional excipients such as carbohydrates, sugars, binders, cryoprotectants, silica, release agents, magnesium stearate, gelatin, and other ingredients well known in the art of tablet and capsule making.

In an exemplary aspect, the invention provides a pharmaceutically acceptable composition comprising cyclosporine-containing microparticles produced by applying energy to particles of cyclosporine in the presence of phospholipid(s) and surface modifier(s). The microparticles consist essentially of cyclosporine (e.g., cyclosporine A), a phospholipid, and at least one surface modifier. The presence of the surface modifier or surface modifiers when the cyclosporine microparticles are formed results in cyclosporine microparticles having a volume-weighted mean particle size that is about 50% smaller than cyclosporine particles produced in the presence of a phospholipid and without the presence of the surface modifier using the same energy input. In another related aspect, the invention provides a process of stabilizing cyclosporine microparticles and preventing particles from aggregating or flocculating by coating or adhering onto the surfaces of the cyclosporine particles a mixture of a phospholipid together with at least one non-ionic, anionic or cationic surfactant, the process comprising the steps of mixing said particles with a phospholipid and at least one non-ionic, anionic or cationic surfactant, and thereafter; applying energy to the mixture sufficient to produce volume-weighted mean particle size values of said compound about 50% smaller than particles produced without the presence of the surfactant using the same energy input.

In another exemplary aspect, the invention provides a pharmaceutical composition comprising fenofibrate-containing microparticles produced by applying energy to fenofibrate in the presence of phospholipid and surface modifier(s), said microparticles consisting essentially of fenofibrate, one or more phospholipids, and at least one surface modifier, in which the surface modifier or surface modifiers provide volume-weighted mean particle size values of the water-insoluble compound about 50% smaller than particles produced in the presence of a phospholipid and without the presence of the surface modifier using the same energy input. In yet another representative aspect, the invention provides a pharmaceutical composition comprising fenofibrate-containing microparticles produced by applying energy to fenofibrate particles in the presence of phospholipid and surfactant surface modifier, said microparticles consisting essentially of fenofibrate, a phospholipid, and a non-ionic, anionic, or cationic surfactant, where the presence of the surfactant (or surfactants) at particle reduction results in fenofibrate-containing microparticles having a volume-weighted mean particle size about 50% smaller than particles produced in the presence of a phospholipid and without the presence of the surfactant using the same energy input.

The compositions of the invention can comprise, consist essentially of, or consist of the materials set forth herein; and the process or method can comprise, consist essentially of, or consist of the steps set forth with such materials.

The following examples further explain and illustrate the invention, but are not meant to be limiting to its scope.

EXAMPLES

Unless otherwise specified, all parts and percentages reported herein are weight per unit volume (w/v), in which the volume in the denominator represents the total volume of the system. Diameters of dimensions are given in millimeters (mm=$10^{-3}$ meters), micrometers (μm=$10^{-6}$ meters), nanometers (nm=$10^{-9}$ meters) or Angstrom units (=0.1 nm). Volumes are given in liters (L), milliliters (mL=$10^{-3}$ L), and microliters (μL=$10^{-6}$ L). Dilutions are given by volume. All temperatures are reported in degrees Celsius.

Example 1

Microparticle-cyclosporine, of an immunosuppressive drug, was prepared as follows. The composition and concentration of excipients of the microparticle cyclosporine formulation are listed below:

| | |
|---|---|
| Cyclosporine | 50 mg/ml |
| Egg Phosphatidylcholine | 100 mg/ml |
| Mannitol | 55 mg/ml |
| Tween 80 | 10 mg/ml |
| Distilled Water | qs to 100% |
| Total Volume | 20 ml |

Cyclosporine with an average particle size from 5-100 μm, and mannitol were purchased from Sigma, egg phosphatidylcholine was produced by Pfanstiehl, Tween 80 was purchased from ICI.

The above components were placed in a 30 ml beaker and pre-mixed with a hand-held biohomogenizer (Honeywell DR 4200 model GP) for 1-5 min. During homogenization, dilute NaOH was added to the pre-mix to adjust the pH from 3.1 to 7±0.5. The pre-mix was placed in a waterjacketed vessel (50 ml capacity) through which thermostated water at 4° C. was circulated to control the temperature of the formulation. The pre-mix was subjected to high shear energy of a probe solicitor (Fisher, model 550 Sonic Dismembrator) with a 0.5 inch diameter probe. Sonic pulses of 10 seconds at 10-seconds intervals at a power setting of 5 were utilized. During sonication the temperature of the formulation was 18±2° C. The pH during sonication was adjusted to 7±0.5 with dilute NaOH. Total sonication time employed to prepare the microparticle cyclosporine was usually 10.5 hours or less. The microparticle-cyclosporine formulation was placed in 20 ml vials and stored at 4° C. and 25° C. for further stability studies.

Particle size distribution of the suspension was analyzed with a NICOMP model 370 Particle Size Analyzer. This instrument utilizes photon correlation spectroscopy for particle sizing in the submicron region. A small volume of the suspension was diluted with water and placed in the cell of the particle size analyzer. Particle size determination based on volume weighted and number weighted particle size determination of the suspension, represented as a Gaussian distribution by the NICOMP 370 software, yielded the mean particle size values, which are listed below in Table 1.

TABLE I

Volume- and Number-Weighted Particle Size Stability of Microparticle-Cyclosporine

| | Storage at 4° C. Mean Particle Size (nm) | | Storage at 25° C. Mean Particle Size (nm) | |
|---|---|---|---|---|
| Storage Time Days | Volume-Weighted | Number-Weighted | Volume-Weighted | Number-Weighted |
| 0 | 461 | 63 | 361 | 63 |
| 7 | 337 | 69 | 423 | 67 |
| 51 | 358 | 76 | 455 | 66 |

Approximately 20 μl of the freshly prepared suspension was placed on a clean slide, with a clean cover glass, and examined under an Olympus BH2 microscope with 1000× magnification. An eye-piece equipped with a graticule was used to estimate the particle size. Most of the particles in the suspension were 0.3 to 0.5 μm. Furthermore, microscopic examination of the suspension confirmed the presence of non-agglomerated or flocculated micron and sub-micron size drug particles exhibiting Brownian motion.

Example 2

For purpose of comparison (not according to the invention) using only a phospholipid, microparticle-cyclosporine with lecithin alone (without the second surface modifier, Tween 80) was also prepared using the same procedure as Example 1. The suspension was stored in 20 ml glass vials for storage stability studies. The volume and number weighted mean particle size values of the suspension stored at 40° C. and 25° C. are listed below. The results in Table II illustrate that the presence of lecithin alone (without the presence of Tween 80) does not provide the particle size reduction and enhancement in storage stability as described in Example 1.

TABLE II

Volume-Weighted Particle Size Stability of Microparticle-Cyclosporine

| | Storage at 4° C. Mean Particle Size (nm) | | Storage at 25° C. Mean Particle Size (nm) | |
|---|---|---|---|---|
| Storage Time Days | Volume-Weighted | Number-Weighted | Volume-Weighted | Number-Weighted |
| 0 | 704 | 91 | 704 | 91 |
| 1 | 1472 | 503 | 2230 | 755 |
| 6 | 1740 | 416 | 2290 | 874 |

Example 3

For purpose of comparison (not according to the invention), a microparticle-cyclosporine composition was prepared using the same procedure as described in Example 1 except that no phospholipid was present during particle size reduction. The suspension was stored in 20 ml glass vials. The results in Table III illustrate that the presence of Tween 80 alone (without the presence of phospholipid) does not provide the level of particle size reduction observed with a combination of phospholipid and surfactant, as described in Example 1.

TABLE III

Volume- and Number-Weighted Particle Size Stability of Microparticle-Cyclosporine

| Days | Mean Particle Size (nm) | |
|---|---|---|
| | Volume-Weighted | Number-Weighted |
| 0 | 521 | 67 |

Example 4

The following microparticle-Docosanol formulations were prepared by the process described in Example 1 using Tween 80 or Tween 20 for the surfactant component and egg phosphatidylcholine, and/or Phospholipon 90H for the phospholipid component. Docosanol was obtained from Sigma. The specific concentration of excipients in the tested microparticle formulations are listed below:

Microparticle-Docosanol (Example 4.1, Comparative)

| | |
|---|---|
| Docosanol | 20 mg/ml |
| Egg Phosphatidylcholine | 50 mg/ml |
| Mannitol | 55 mg/ml |
| Distilled Water | qs to 100% |
| Total Volume | 20 ml |

Microparticle-Docosanol (Example 4.2)

| | |
|---|---|
| Docosanol | 20 mg/ml |
| Egg Phosphatidylcholine | 50 mg/ml |
| Mannitol | 55 mg/ml |
| Tween 80 | 10 mg/ml |
| Distilled Water | qs to 100% |
| Total Volume | 20 ml |

Microparticle-Docosanol (Example 4.3)

| | |
|---|---|
| Docosanol | 20 mg/ml |
| Egg Phosphatidylcholine | 50 mg/ml |
| Mannitol | 55 mg/ml |
| Tween 20 | 10 mg/ml |
| Distilled Water | qs to 100% |
| Total Volume | 20 ml |

Microparticle-Docosanol (Example 4.4)

| | |
|---|---|
| Docosanol | 20 mg/ml |
| Phospholipon 90H | 30 mg/ml |
| Mannitol | 55 mg/ml |
| Tween 80 | 10 mg/ml |
| Distilled Water | qs to 100% |
| Total Volume | 20 ml |

Microparticle-Docosanol (Example 4.5, Comparative)

| | |
|---|---|
| Docosanol | 20 mg/ml |
| Mannitol | 55 mg/ml |
| Tween 80 | 10 mg/ml |
| Distilled Water | qs to 100% |
| Total Volume | 20 ml |

The mean volume- and number-weighted particle size values of the suspension were 286 nm, and 98 nm, respectively.

The volume-weighted mean particle size values of the above-described suspensions, stored at 4° C., are listed below in Table IV.

TABLE IV

Volume-Weighted and Number-Weighted Particle Size Stability of Microparticle-Docosanol Stored at 4° C.

| | (Example 4.1) Mean Particle Size (nm) | | (Example 4.2) Mean Particle Size (nm) | |
|---|---|---|---|---|
| Storage Time Days | Volume-Weighted | Number-Weighted | Volume-Weighted | Number-Weighted |
| 0 | 688 | — | 112 | 55 |
| 30 | ND | ND | 156 | 81 |

| | (Example 4.3) Mean Particle Size (nm) | | (Example 4.4) Mean Particle Size (nm) | |
|---|---|---|---|---|
| Storage Time Days | Volume-Weighted | Number-Weighted | Volume-Weighted | Number-Weighted |
| 0 | 129 | 61 | 90 | 35 |
| 30 | 184 | 99 | 127 | 39 |

ND = Not Determined

The data presented above illustrate that much smaller particles are produced in of a surfactant and a phospholipid as compared to the phospholipid alone and that particles produced in accordance with the invention retain their particle size over time without significant increase in size.

Example 5

The following seven microparticle-RTP-4055 (an antiviral drug) formulations were prepared with combinations of Tween 80, Tetronic 908, Pluronic F-68, egg phosphatidylcholine, and/or Phospholipon 90H as surface modifiers. The details of the sonication method are similar to those discussed in Example 1. The composition and concentration of excipients of the microparticle formulations are listed below:

Microparticle-RTP-4055 (Example 5.1, Comparative)

| | |
|---|---|
| RTP-4055 | 50 mg/ml |
| Egg Phosphatidylcholine | 50 mg/ml |
| Distilled Water | qs to 100% |
| Total Volume | 25 ml |

The mean volume-weighted particle size of the suspension was 3195 mn.

Microparticle-RTP-4055 (Example 5.2)

| | |
|---|---|
| RTP-4055 | 50 mg/ml |
| Egg Phosphatidylcholine | 50 mg/ml |
| Mannitol | 55 mg/ml |
| Pluronic F-68 | 5 mg/ml |
| Distilled Water | qs to 100% |
| Total Volume | 25 ml |

The mean volume- and number-weighted particle size values of the suspension were 672 nm and 76 nm respectively.
Microparticle-RTP-4055 (Example 5.3)

| | |
|---|---|
| RTP-4055 | 50 mg/ml |
| Egg Phosphatidylcholine | 50 mg/ml |
| Mannitol | 55 mg/ml |
| Tetronic 908 | 5 mg/ml |
| Distilled Water | qs to 100% |
| Total Volume | 25 ml |

The mean volume- and number-weighted particle size values of the suspension were 436 nm and 59 nm respectively.
Microparticle-RTP-4055 (Example 5.4, Comparative)

| | |
|---|---|
| RTP-4055 | 50 mg/ml |
| Phospholipon 90H | 30 mg/ml |
| Distilled Water | qs to 100% |
| Total Volume | 25 ml |

The mean volume- and number-weighted particle size values of the suspension were 1117 nm and 108 nm respectively.
Microparticle-RTP-4055 (Example 5.5)

| | |
|---|---|
| RTP-4055 | 50 mg/ml |
| Phospholipon 90H | 30 mg/ml |
| Mannitol | 55 mg/ml |
| Dimyristoylphosphatidyl choline (DMPG) | 3 mg/ml |
| Tween 80 | 10 mg/ml |
| Distilled Water | qs to 100% |
| Total Volume | 25 ml |

The mean volume weighted particle size of the suspension was 236 nm. The mean volume weighted particle size of the suspension stored at 4° C. for 1 week and 1 month are 328 and 397 nm, respectively, which indicates the stability of the suspension.
Microparticle-RTP-4055 (Example 5.6)

| | |
|---|---|
| RTP-4055 | 50 mg/ml |
| Phospholipon 90H | 30 mg/ml |
| Mannitol | 55 mg/ml |
| Tween 80 | 10 mg/ml |
| Distilled Water | qs to 100% |
| Total Volume | 25 ml |

The mean volume- and number-weighted mean particle size values of the suspension were 382 nm and 59 nm, respectively. Within the error limits, there was no variation in the mean particle size after one week of storage at 4° C.
Microparticle-RTP-4055 (Example 5.7, Comparative)

| | |
|---|---|
| RTP-4055 | 50 mg/ml |
| Mannitol | 55 mg/ml |
| Tween 80 | 10 mg/ml |
| Distilled Water | qs to 100% |
| Total Volume | 25 ml |

The mean volume- and number-weighted mean particle size values of the suspension were 545 nm, and 75 nm, respectively within the error limits, there was no variation in the mean particle size after one week of storage at 4° C.

Example 6

The following six microparticle-Piroxicam formulations were prepared with combination of Tween 80, Tetronic 908, Pluronic F-68, and/or egg phosphatidylcholine as surface modifiers. Piroxicam was received from Cipla. The details of the sonication method are similar to those discussed in Example 1. The compositions and concentration of excipients of the microparticle formulations are listed below:
Microparticle-Piroxicam (Example 6.1)

| | |
|---|---|
| Piroxicam | 67 mg/ml |
| Egg Phosphatidylcholine | 67 mg/ml |
| Mannitol | 67 mg/ml |
| Tween 80 | 5 mg/ml |
| Tetronic 908 | 5 mg/ml |
| Distilled Water | qs to 100% (w/v) |
| Total Volume | 15 ml |

The mean volume- and number-weighted particle size values of the suspension were 674 nm and 72 nm, respectively.
Microparticle-Piroxicam (Example 6.2)

| | |
|---|---|
| Piroxicam | 67 mg/ml |
| Egg Phosphatidylcholine | 67 mg/ml |
| Mannitol | 67 mg/ml |
| Tetronic 908 | 5 mg/ml |
| Distilled Water | qs to 100% (w/v) |
| Total Volume | 15 ml |

The mean volume- and number-weighted particle size values of the suspension were 455 nm and 58 nm, respectively.
Microparticle-Piroxicam (Example 6.3)

| | |
|---|---|
| Piroxicam | 67 mg/ml |
| Egg Phosphatidylcholine | 67 mg/ml |
| Mannitol | 67 mg/ml |
| Pluronic F-68 | 5 mg/ml |
| Distilled Water | qs to 100% (w/v) |
| Total Volume | 15 ml |

The mean volume- and number-weighted particle size values of the suspension were 564 nm and 68 nm, respectively.
Microparticle-Piroxicam (Example 6.4)

| | |
|---|---|
| Piroxicam | 67 mg/ml |
| Egg Phosphatidylcholine | 67 mg/ml |
| Mannitol | 67 mg/ml |
| Tween 80 | 5 mg/ml |
| Cetyltrimethylammonium bromide | 10 mg/ml |
| Distilled Water | qs to 100% (w/v) |
| Total Volume | 15 ml |

The mean volume- and number-weighted particle size values of the suspension were 479 nm and 80 nm, respectively.

Microparticle-Piroxicam (Example 6.5)

| | |
|---|---|
| Piroxicam | 67 mg/ml |
| Egg Phosphatidylcholine | 67 mg/ml |
| Mannitol | 67 mg/ml |
| Cetyltrimethylammonium bromide | 10 mg/ml |
| Distilled Water | qs to 100% (w/v) |
| Total Volume | 15 ml |

The mean volume- and number-weighted particle size values of the suspension were 670 nm and 128 mn, respectively.

Microparticle-Piroxicam (Example 6.6, Comparative)

| | |
|---|---|
| Piroxicam | 67 mg/ml |
| Mannitol | 67 mg/ml |
| Tween 80 | 5 mg/ml |
| Tetronic 908 | 5 mg/ml |
| Distilled Water | qs to 100% |
| Total Volume | 15 ml |

The mean volume- and number-weighted particle size values of the suspension were 1184 nm and 385 nm, respectively.

Examples 7-12

Microparticies of cyclosporine were prepared in a microfluidizer (Microfluidics—Newton, Mass. (USA)) to examine the effect in particle size due to the presence or absence of surfactant, (Examples 7 and 8 (comparative) vs. Examples 9, 10 and 11), the use of a phospholipid having a high phospholipidal choline content (Example 9 vs. Examples 10 and 11) and mixtures of two solid surfactants (Example 10 vs. Example 11). The method of preparing the compositions corresponding to these Examples is the same as Example 1, except that microfluidization, rather than by sonication, was used to reduce the size of the cyclosporine particles.

Cyclosporine was purchased from North China Pharmaceutical Corporation. P123 egg phospholipid or Phospholipon 100H were used for the phospholipid component in the test compositions. P123 egg phospholipid (Pfansiehl), is a waxy substance that contains about 70% phosphatidylcholine, while Phospholipon 100H (Natterman), a hydrogenated soy lecithin, contains more than 90% phosphatidylcholine. Phospholipon 100H is a free flowing powder, while Pfanstiehl P123 is a waxy substance.

Tween 80, Myri 52, and sodium deoxycholate were variously used for the surfactant component. Tween 80 was purchased from ICI, Myri 52 was purchased from ICT, and sodium deoxycholate was purchased from Perdotti Chimici E. Alimentari S.P.A.

The specific amounts of ingredients for the test compositions are reported in Table V as percent by weight, balance water.

TABLE V

| | Example | | | | | |
|---|---|---|---|---|---|---|
| | 7 | 8 | 9 | 10 | 11 (Batch 1) | 12 |
| Cyclosporine | 5% | 5% | 5% | 5% | 5% | 5% |
| Pfanstiehl egg phospholipid | 10% | | 10% | | 10% | 0% |
| Phospholipon 100H | | 2% | | 2% | | |
| Tween 80 | | | 2% | 2% | | |
| Myri 52 | | | | | 1% | 2% |
| Sodium deoxycholate | | | | | 0.25% | |
| Mannitol | 5.5% | 5.5% | 5.5% | 5.5% | 5.5% | 5.5% |
| Mean volume weighted particle size (microns) | 3.34 | 13.57 | 1.14 | 0.64 | 0.74 | 0.75 |

The formulation of Example 9 is the same as that of Example 1 but was produced using a microfluidizer rather than by sonication.

Examples 7 and 8 are not according to the invention, as they lack surfactants. The relatively significantly larger particle size obtained with the corresponding compositions reflects this fact.

Purer lipids were found to be less susceptible to hydrolysis (dehydration).

Formulations containing Pfanstiehl P123 did not always form free flowing powders. Tween 80, a viscous liquid, upon lyophilization produces a powder having a slightly sticky touch and did not always form suitably free flowing powders, whereas Myri 52 and sodium deoxycholate, both solids, produced free flowing powders.

Sodium deoxycholate is a bile salt. It is thought that absorption of cyclosporine products is dependent upon solubilization of bile salts, thus sodium deoxycholate may enhance cyclosporine uptake.

The combination of surfactants in Example 11 was found to aid in reduction of particle size and stability and manufacturability of the product. The product of Example 11 (batch 2) remained remarkably stable on storage (e.g., at the initial (0) time average particle size was 0.92 μm, and after four months particle size was only 0.95 μm).

The combination of two second surfactants together with a phospholipid unexpectedly and enhanced the reduction of particle size, increased particle size stability. For example, in Example 11, the combination of two second surfactants, Myri 52 and sodium deoxycholate, together with an egg phospholipid, Pfanstiehl egg phospholipid, was found to unexpectedly significantly enhance the reduction of particle size and increase particle size stability as compared to the Examples not of the invention.

The difference in volume-weighted mean particle size of the cyclosporin microparticles in Examples 9 and 7 is characterized by a ratio of 1.14/3.34. Thus, the particles of solid cyclic oligopeptide cyclosporine of Example 9, prepared with phospholipid together with a second surfactant, Tween 80, were found, unexpectedly, to be more than 50% smaller than the particles of solid cyclic oligopeptide cyclosporine prepared with phospholipid alone using the same energy input.

The volume weighted mean particle size of the cyclosporine microparticles obtained in Examples 10 and 8 differ by a ratio of 0.64/13.57. Thus, the particles of solid cyclic oligopeptide cyclosporine of Example 10, which were prepared with phospholipid together with a second surfactant, Tween 80, were found, unexpectedly, to be more than 50% smaller than the particles of solid cyclic oligopeptide cyclosporine prepared with phospholipid alone by application of the same energy input.

The volume weighted mean particle size of particles of solid cyclic oligopeptide cyclosporine obtained in Examples 11 and 7 differ by a ratio of 0.74/3.34. Therefore, the particles of solid cyclic oligopeptide cyclosporine of Example 11, prepared with phospholipid together with two second surfactants, Myri 52 and sodium deoxycholate, also were unexpectedly more than 50% smaller than the particles of solid cyclic oligopeptide cyclosporine prepared with phospholipid without the presence of the second surfactants by application of the same energy input used to produce the cyclosporine microparticles of Example 11.

Example 13

This example demonstrates the bioavailability of solid cyclic oligopeptide cyclosporine particles, produced by the method of the invention, relative to commercially available Neoral® microemulsion capsules.

Bioavailability of various suspensions was assessed in male volunteers and values obtained were reported relative to Neoral® capsules of microemulsion (Novartis). Results are as follows:

TABLE VI

|  | Example 9 | Example 11 | Example 12* |
|---|---|---|---|
| $AUC_{0-inf}$ | 0.97 | 0.91 | 0.86 |
| Cmax | 0.79 | 0.84 | 0.84 |
| Particle Size ** | 0.67 micron | 1.35 micron **** | 0.75 micron |
| Particle Size *** | 0.58 micron | 0.47 micron | 0.72 micron |

* Example 12 = Example 11 but modified to include 2% Myri 52 and no sodium deoxycholate
** Volume weighted particle size D[4, 3]
*** D50% value
**** Process intentionally terminated at this particle size

Examples 14-19

The following microparticle-fenofibrate formulations were prepared either by using Microfluidizer® model 110EH (Microfluidics Corp., Newton, Mass.) or Avestin model C5 (Ottawa, Canada).

A premix of the formulation was prepared by placing the ingredients in an appropriate size vessel with the required amount of water and mixed with a hand held homogenizer. The premix so formed was then placed in the inlet reservoir of the homogenizer and passing the outlet flow through a thermostatically controlled cooler to control the inlet temperature. The premix was then pumped through the homogenizer at 18,000-20,000 psi. The homogenization process can either be done by discrete passes or in continuous mode. For the sake of comparison, all formulations (except Example 13) were homogenized for 90 passes in Avestin homogenizer. The formulation in Example 13 was prepared in a Microfluidizer® with using approximately 50 passes at full pressure. The formulations were harvested and particle size and other parameters measured. The particle size determination was performed with Malvern Mastersizer model Micro-Plus (Southborough, Mass.). The particle size data are presented as volume weighted mean particle size.

The composition and concentration of excipients of the various tested microparticle fenofibrate formulations are listed below. The amount of excipients used is expressed as percent (w/w):

Example 14

| | |
|---|---|
| Fenofibrate | 10.0 |
| Phospholipon 100H | 2.0 |
| Tween 80 | 2.0 |
| Mannitol | 5.5 |
| Mean particle size: | 0.85 μm |

Example 15

| | |
|---|---|
| Fenofibrate | 10.0 |
| Phospholipon 100H | 2.0 |
| Tween80 | 2.0 |
| Mannitol | 10.0 |
| Mean particle size: | 1.02 μm |

Example 16

| | |
|---|---|
| Fenofibrate | 10.0 |
| Phospholipon 100H | 2.0 |
| PVP 30 | 1.5 |
| Mannitol | 5.5 |
| Mean particle size: | 1.28 μm |

Example 17

| | |
|---|---|
| Fenofibrate | 10.0 |
| Phospholipon 100H | 2.0 |
| Myrj 52 | 1.5 |
| Mannitol | 5.5 |
| Mean particle size: | 1.21 μm |

Example 18

| | |
|---|---|
| Fenofibrate | 10.0 |
| Phospholipon 100H | 2.0 |
| Poloxamer 188 | 1.5 |
| Mannitol | 5.5 |
| Mean particle size: | 1.12 μm |

For the purpose of comparison (not according to the invention), fenofibrate particles were also prepared using only a phospholipid, (without the surfactant, Tween 80), by the same procedure as Example 14:

Example 19(Comparative)

| Fenofibrate | 10.0 |
|---|---|
| Phospholipon 100H | 2.0 |
| Mannitol | 5.5 |
| Mean particle size: | 3.17 μm |

A comparison of the resulting mean particles size of the final formulations in Examples 14 to 18, inclusive, with the corresponding values for the formulation of Example 19, demonstrate the effect of adding the second surface modifier on the final particle size. Also, it was observed that the use of a second surface modifier helps to eliminate the thick slurry produced when Phospholipon 100H is used alone.

Example 20

This example demonstrates the superior bioavailability of fenofibrate microparticles of the invention administered orally to human subjects.

The Fenofibrate composition used in Example 15 (above) was tested in a human volunteers study. The study consisted of oral administration of the fenofibrate formulation to eight human volunteers in a single dose crossover design, using the marketed formulation as a reference. The dose administered was 67 mg. Blood samples were collected before and after each administration at various time points over 120 hours.

The drug concentration in blood samples was determined by high-pressure liquid chromatography by monitoring for the level of the metabolite, fenofibric acid. The pharmacokinetic results are presented in Table VI and demonstrate the superior bioavailability of the fenofibrate formulation prepared according to the inventive method over the commercially available product.

TABLE VII $C_{max}$ and $AUC_{0}$-inf for Fenofibric Acid

| | $C_{max}$ (ng · ml − 1) | $AUC_{0\text{-}inf}$ (ng · ml$^{-1}$ · h) |
|---|---|---|
| Fenofibrate microparticles (67 mg) | 2528 | 57235 |
| Commercially available fenofibrate (67 mg) product | 1372 | 38629 |
| Dunnett's t-test (log transformed data) | $p < 0.05$ | $p < 0.05$ |

What is claimed is:

1. A process for preparing solid microparticles of a water-insoluble or poorly water-soluble compound in an aqueous medium, which process consists essentially of:
   (a) adding particles of the water-insoluble or poorly water-soluble compound with at least one phospholipid and at least one surfactant that is not a phospholipid to a container to form a pre-mixture;
   (b) homogenizing the pre-mixture;
   (c) sonicating the pre-mixture to produce stable solid microparticles at a temperature between 16° C.-20° C.; and
   (d) adjusting the pH of the mixture during step b, step c or during both steps b and c~wherein said water-insoluble or poorly water-soluble compound is a drug.

2. The process of claim 1, wherein the at least one surfactant consists of two or more surfactants, the at least one phospholipid consists of two or more phospholipids, or the at least one surfactant consists of two or more surfactants and the at least one phospholipid consists of two or more phospholipids.

3. The process of claim 1, wherein the at least one surfactant comprises (a) one or more cationic surfactants; (b) one or more nonionic surfactants; (c) an anionic surfactant selected from the group consisting of sodium dodecylsulfate, sodium deoxycholate, dioctyl sodium sulfosuccinate, potassium laurate, sodium lauryl sulfate, an alkyl polyoxyethylene sulfate, sodium alginate, a negatively charged glyceryl ester, and combinations thereof; or (d) a combination of such cationic, nonionic, and/or anionic surfactants.

4. The process of claim 1, wherein average particle size of said stable microparticles of after four months is about 1.033× the particle size of said particle when formed.

5. A process for preparing solid microparticles of a water-insoluble or poorly water-soluble compound in an aqueous medium, which process consists essentially of:
   (a) adding particles of the water-insoluble or poorly water-soluble compound with at least one phospholipid and at least one surfactant that is not a phospholipid to a container to form a pre-mixture;
   (b) homogenizing the pre-mixture;
   (c) microfluidizing the pre-mixture to produce stable solid microparticles at a temperature between 16° C.-20° C.; and
   (d) adjusting the pH of the mixture during step b, step c or during both steps b and c~wherein said water-insoluble or poorly water-soluble compound is a drug.

6. The process of claim 5, wherein the process comprises precipitating the particles of the water-insoluble or poorly water-soluble compound in the presence of the at least one phospholipid and the at least one surfactant, followed by subjecting the precipitated particles, the at least one phospholipid, and the at least one surfactant to microfluidization.

7. The process of claim 6, wherein the at least one phospholipid comprises one or more synthetic phospholipids, semisynthetic phospholipids, phospholipids of egg or plant origin, or a combination of any thereof.

8. The process of claim 7, wherein the at least one phospholipid comprises one or more phospholipids selected from the group consisting of phosphatidylcholine, phosphatidylethanolamine, phosphatidylserine, phosphatidylinositol, phosphatidyiglycerol, dimyristoyl phosphatidylglycerol sodium salt, phosphatidic acid, lysophospholipids, and combinations thereof.

9. The process of claim 8, wherein the at least one phospholipid includes phosphatidylcholine.

10. The process of claim 9, wherein the at least one phospholipid consists of egg phosphatidyicholine.

11. The process of claim 7, wherein the at least one phospholipid includes at least one phospholipid in desalted or salt form.

12. The process of claim 7, wherein the at least one phospholipid includes at least one phospholipid in fully hydrogenated or partly hydrogenated form.

13. The process of claim 6, wherein the process comprises formulating the microparticles for oral, inhalation, ocular, nasal, or injectable administration.

14. The process of claim 13, wherein the process comprises formulating the microparticles in the form of an aqueous suspension.

15. The process of claim 5, wherein the at least one surfactant comprises one or more nonionic surfactants.

16. The process of claim 5, wherein the at least one surfactant comprises one or more surfactants selected from the group consisting of poloxamers, poloxamines, sorbitan esters, alkyl aryl polyether sulfonates, polyethylene glycols, sodium dodecylsulfate, sodium deoxycholate, cholesterol esters, glycerol monostearate, cetyl alcohol, cetostearyl alcohol, stearyl alcohol, polyoxyethylene fatty acid esters, polyvinyl alcohol, potassium laurate, triethanolamine stearate, polyvinylpyrrolidone, alkyl polyoxyethylene sulfates, dioctyl sodium sulfosuccinate, negatively charged glyceryl esters, quaternary ammonium cationic surfactants, chitosans, and combinations thereof.

17. The process of claim 16, wherein the at least one surfactant comprises one or more quaternary ammonium cationic surfactants selected from the group consisting of benzalkonium chloride, lauryldimethylbenzylammonium chloride, cetyltrimethylammonium bromide, and combinations thereof.

18. The process of claim 16, wherein the at least one surfactant comprises one or more sorbitan fatty esters.

19. The process of claim 18, wherein the at least one surfactant comprises one or more polyoxyethylene sorbitan fatty acid esters.

20. The process of claim 16, wherein the at least one surfactant comprises polyoxyethylene stearate.

21. The process of claim 16, wherein the at least one surfactant comprises a block copolymer of ethylene oxide and propylene oxide.

22. The process of claim 5, wherein the at least one surfactant comprises a surfactant selected from the group consisting of casein, gelatin, tragacanth, acacia, cholesterol, and combinations thereof.

23. The process of claim 5, wherein the mean particle size of the microparticles is at least 50% smaller than the mean particle size of particles of the water-insoluble or poorly water-soluble compound produced by subjecting a mixture of the particles of the water insoluble or poorly water-soluble compound and a phospholipid, without the at least one surfactant, to precipitation, microfluidization, or precipitation and microfluidization, applying the same energy input used to produce the microparticles.

24. The process of claim 5, wherein the water-insoluble or poorly water-soluble compound is selected from the group consisting of an immunosuppressive agent, an immunoactive agent, an antiviral agent, an antifungal agent, an antineoplastic agent, an analgesic agent, an antiinflammatory agent, an antibiotic, an anti-epileptic agent, an anesthetic, a hypnotic, a sedative, an antipsychotic agent, a neuroleptic agent, an antidepressant, an anxiolytic, an anticonvulsant agent, an antagonist, a neuron blocking agent, an anticholinergic agent, a cholinomimetic agent, an antimuscarinic agent, a muscarinic agent, an antiadrenergic, an antiarrhythmic, an antihypertensive agent, a hormone, and combinations thereof.

25. The process of claim 24, wherein the water-insoluble or poorly water-soluble compound is an antifungal agent.

26. The process of claim 5, wherein the at least one surfactant comprises at least one surfactant in a concentration above its critical micelle concentration.

27. The process of claim 5, wherein the particles of the water-insoluble or poorly water-soluble compound are 5-100 µm size.

28. The process of claim 5, wherein the process comprises reducing the size of the particles of the water-insoluble or poorly water-soluble compound by antisolvent/solvent precipitation.

29. The process of claim 5, wherein the process comprises reducing the size of the particles of the water-insoluble or poorly water-soluble compound by precipitation from supercritical fluids.

30. The process of claim 5, wherein the process comprises formulating the microparticles for oral, inhalation, ocular, nasal, or injectable administration.

31. The process of claim 30, wherein the process comprises formulating the microparticles in injectable form for intravenous, intra-arterial, intra-muscular, intradermal, subcutaneous, intra-articular, cerebrospinal, epidural, intracostal, intraperitoneal, intratumor, intrabladder, intra-lesion, or subconjunctival administration.

32. The process of claim 5, wherein the process comprises drying the microparticles.

33. The process of claim 32, wherein the process comprises drying the microparticles by lyophilization, fluid drying, or spray drying.

34. The process of claim 32, wherein the process comprises drying the microparticles in the presence of a stabilizing agent.

35. The process of claim 34, wherein the stabilizing agent is mannitol.

36. A process for preparing solid microparticles of a water-insoluble or poorly water-soluble compound in an aqueous medium, the process consisting essentially of:
   (1) adding solid particles of a water-insoluble or poorly water-soluble compound with at least one phospholipid and at least one surfactant that is not a phospholipid to a container to form a pre-mixture prior to forming a dispersion, wherein the pre-mixture;
   (2) homogenizing the pre-mixture;
   (3) applying energy to the mixture sufficient to produce stable solid microparticles of the compound at a temperature of between 16° C.-20° C., wherein applying energy includes subjecting the mixture to sonication, homogenization, milling, microfluidization, precipitation, recrystallization or combination thereof; and
   (4) adjusting the pH of the mixture during step 2, step 3 or during both steps 2 and 3~wherein said water-insoluble or poorly water-soluble compound is a drug.

37. The process of claim 36, wherein applying energy includes subjecting the mixture to precipitation, microfluidization, or precipitation and microfluidization.

38. The process of claim 36, wherein the at least one surfactant is present in a concentration above its critical micelle concentration.

39. The process of claim 36, wherein the at least one phospholipid is selected from the group consisting of phosphatidylcholine, phosphatidylethanolamine, phosphatidylserine, phosphatidylinositol, phosphatidyiglycerol, dimyristoyl phosphatidyiglycerol sodium salt, phosphatidic acid, lysophospholipids, and combinations thereof.

40. The process of claim 36, wherein the at least one surfactant consists of two or more surfactants, the at least one phospholipid consists of two or more phospholipids, or the at least one surfactant consists of two or more surfactants and the at least one phospholipid consists of two or more phospholipids.

41. The process of claim 36, wherein the at least one surfactant is one or more nonionic surfactants.

42. The process of claim 36, wherein the particles of the water-insoluble or poorly water-soluble compound are 5-100 μm in size.

43. The process of claim 36, wherein the process comprises drying the microparticles.

44. The process of claim 43, wherein the process comprises drying the microparticles by lyophilization, fluid dying, or spray drying.

45. The process of claim 43, wherein the process comprises drying the microparticles in the presence of a stabilizing agent.

46. The process of claim 45, wherein the stabilizing agent is mannitol.

47. A composition comprising stable solid microparticles of a water-insoluble or poorly water-soluble compound, at least one phospholipid, and at least one surfactant, produced by adding particles of the water-insoluble or poorly water-soluble compound with the at least one phospholipid and the at least one surfactant to a container to form a pre-mixture prior to forming a dispersion; wherein the pre-mixture is formed and is homogenized, and applying an energy to the mixture so as to obtain the microparticles, wherein the energy includes subjecting the mixture to sonication, homogenization, milling, microfluidization, precipitation, recrystallization or combination thereof at a temperature better 16° C.-20° C. and wherein the at least one surfactant is not a phospholipid and
    (a) the volume-weighted mean particle size of the microparticles after one week of storage in an aqueous medium at 4-25° C. is less than 50% more than the volume-weighted mean particle size of the microparticles before storage,
    (b) the volume-weighted mean particle size of the microparticles after six days of storage is about 80% smaller than the volume-weighted mean particle size of particles of the water-insoluble or poorly water-soluble compound produced without the presence of the at least one surfactant by applying the same energy input, or
    (c) the volume-weighted mean particle size of the microparticles after one week of storage in an aqueous medium at 4-25° C. is less than 50% more than the volume-weighted mean particle size of the microparticles before storage and the volume-weighted mean particle size of the microparticles after six days of storage is about 80% smaller than the volume-weighted mean particle size of particles of the water-insoluble or poorly water-soluble compound produced without the presence of the at least one surfactant by applying the same energy input, wherein said water-insoluble or poorly water-soluble compound is a drug.

48. The composition of claim 47, wherein the microparticles exhibit no detectable increase in volume-weighted mean particle size when stored for one week at 4° C.

49. A process for preparing solid microparticles of a water-insoluble or poorly water-soluble compound which process consists essentially of:
    (a) adding particles of the water-insoluble or poorly water-soluble drug with at least one phospholipid and at least one surfactant to a container to form a pre-mixture prior to forming a dispersion;
    (b) subjecting the mixture to precipitation, microfluidization, or precipitation and microfluidization to produce stable solid microparticles at a temperature 16° C.-20° C.; and
    (c) adjusting the pH of the mixture during step a, step b or during both steps a and b wherein the at least one surfactant is not a phospholipid, wherein said water-insoluble or poorly water-soluble compound is a drug.

50. A process for preparing solid microparticles of a water-insoluble or poorly water-soluble compound in an aqueous medium, which process comprises:
    (a) adding particles of the water-insoluble or poorly water-soluble compound with at least one phospholipid and at least one surfactant that is not a phospholipid to a container to form a pre-mixture;
    (b) homogenizing the pre-mixture;
    (c) sonicating the pre-mixture to produce solid microparticles at a temperature between 16° C.-20° C.; and
    (d) adjusting the pH of the mixture during step b, step c or during both steps b and c~wherein said water-insoluble or poorly water-soluble compound is a drug.

51. A process for preparing solid microparticles of a water-insoluble or poorly water-soluble compound in an aqueous medium, which process comprises:
    (a) adding particles of the water-insoluble or poorly water-soluble compound with at least one phospholipid and at least one surfactant that is not a phospholipid to a container to form a pre-mixture;
    (b) homogenizing the pre-mixture;
    (c) microfluidizing the pre-mixture to produce solid microparticles at a temperature between 16° C.-20° C.; and
    (d) adjusting the pH of the mixture during step b, step c or during both steps b and c, wherein said water-insoluble or poorly water-soluble compound is a drug.

52. A process for preparing solid microparticles of a water-insoluble or poorly water-soluble compound in an aqueous medium, the process comprises:
    (1) adding solid particles of the water-insoluble or poorly water-soluble compound with at least one phospholipid and at least one surfactant that is not a phospholipid to a container to form a pre-mixture prior to forming a dispersion;
    (2) homogenizing the pre-mixture;
    (3) applying energy to the mixture sufficient to produce solid microparticles of the compound at a temperature of between 16° C.-20° C., wherein applying energy includes subjecting the mixture to sonication, homogenization, milling, microfluidization, precipitation, recrystallization or combination thereof; and
    (4) adjusting the pH of the mixture during step 2, step 3 or during both steps 2 and 3, wherein said water-insoluble or poorly water-soluble compound is a drug.

53. A process for preparing solid microparticles of a water-insoluble or poorly water-soluble compound which process consists of:
    (a) adding particles of the water-insoluble or poorly water-soluble drug with at least one phospholipid and at least one surfactant to a container to form a pre-mixture prior to forming a dispersion, and wherein the mixture is formed and homogenized;
    (b) subjecting the mixture to precipitation, microfluidization, or precipitation and microfluidization to produce solid microparticles at a temperature of between 16° C.-20° C.; and
    (c) adjusting the pH of the mixture during step a, step b or during both steps a and b wherein the at least one surfactant is not a phospholipid,
    wherein said water-insoluble or poorly water-soluble compound is a drug.

* * * * *